United States Patent [19]

Ogilive

[11] Patent Number: 5,480,425
[45] Date of Patent: Jan. 2, 1996

[54] INTEGRATED HEART VALVE ROTATOR AND HOLDER

[75] Inventor: William F. Ogilive, Austin, Tex.

[73] Assignee: CarboMedics, Inc., Austin, Tex.

[21] Appl. No.: 257,681

[22] Filed: Jun. 9, 1994

[51] Int. Cl.⁶ .................................................... A61F 2/24
[52] U.S. Cl. .......................... 623/2; 623/3; 606/1; 606/99
[58] Field of Search ................................ 623/2, 3; 606/1, 606/99, 108

[56] References Cited

U.S. PATENT DOCUMENTS

| | | | |
|---|---|---|---|
| 3,860,005 | 1/1975 | Anderson et al. | 623/2 |
| 4,065,816 | 1/1978 | Sawyer | 623/2 |
| 4,182,446 | 1/1980 | Penny | 206/205 |
| 4,185,636 | 1/1980 | Gabbay et al. | 128/334 R |
| 4,197,593 | 4/1980 | Kaster et al. | 623/2 |
| 4,211,325 | 7/1980 | Wright | 206/438 |
| 4,585,453 | 4/1986 | Martin et al. | 623/2 |
| 4,655,218 | 4/1987 | Kulik et al. | 128/321 |
| 4,679,556 | 7/1987 | Lubock et al. | 623/2 |
| 4,683,883 | 8/1987 | Martin | 128/303 R |
| 4,683,883 | 8/1987 | Martin | 623/2 |
| 4,702,250 | 10/1987 | Ovil et al. | 128/334 R |
| 4,755,181 | 7/1988 | Igoe | 623/2 |
| 4,865,600 | 10/1989 | Carpentier et al. | 623/2 |
| 4,878,494 | 11/1989 | Phillips et al. | 128/334 R |
| 4,932,965 | 7/1990 | Phillips | 623/2 |
| 5,011,481 | 4/1991 | Myers et al. | 623/2 |
| 5,041,130 | 8/1991 | Cosgrove et al. | 623/2 |
| 5,071,431 | 12/1991 | Sauter et al. | 623/2 |
| 5,163,955 | 11/1992 | Love et al. | 623/2 |
| 5,197,979 | 3/1993 | Quintero et al. | 623/2 |
| 5,236,450 | 8/1993 | Scott | 623/2 |

*Primary Examiner*—David H. Willse
*Assistant Examiner*—Bruce E. Snow
*Attorney, Agent, or Firm*—John R. Merkling

[57] ABSTRACT

An integrated heart valve rotator and holder comprising a central rotator which is used, first, to protect and stabilize the leaflets of the heart valve during implantation and, second, to rotate the heart valve into a desired position after the sewing ring has been attached. A heart valve holder mounts on the rotator and is secured to the heart valve suture ring by a thread or suture. After the heart valve is stitched into the proper location in the heart, the attending physician cuts the suture at a single location and withdraws the heart valve holder, rotator and suture as a single component. The heart valve holder, carrying both parts of the severed suture, is removed from the rotator. The rotator can then be returned to the heart valve to adjust the orientation of the annular valve body within the suture ring.

11 Claims, 1 Drawing Sheet

INTEGRATED HEART VALVE ROTATOR AND HOLDER

FIELD OF MY INVENTION

My invention relates to mechanical prosthetic heart valves, and particularly to apparatus for holding such heart valves during surgical implantation in the heart of the patient.

BACKGROUND OF MY INVENTION

Prosthetic heart valves fall generally into two categories: mechanical heart valves and bioprosthetic heart valves. Mechanical heart valves are conventionally constructed with a rigid annular body supporting one, two, or more leaflets. The action of these leaflets in opening and closing controls the flow of blood through the valve. The annular body of the heart valve is secured in a sewing ring, a structure which is usually comprised of Dacron (TM) or some other biocompatible material which permits a surgeon to stitch the valve into a location in the heart. Holding the valve in position while implantation takes place has been and remains a problem for which new solutions are sought. One solution has been a holder for the heart valve which has two opposite substantially mirror image halves which are joined by a pin or hinge. Adjacent the heart valve, two jaws operate outwardly to engage the heart valve from the inside. This has been a generally satisfactory configuration in many instances.

Mechanical prosthetic heart valves have also been developed which have rotatable sewing rings, that is, the annular body can be rotated within the sewing ring. More recently, valves have been made wherein the annular body can rotate with little resistance. If a hinged valve holder is used with the latter valves, the sewing ring is still free to rotate during implantation. This adversely affects implantation.

SUMMARY OF MY INVENTION

I have invented an integrated heart valve rotator and holder which can both rotate an annular valve body and secure a sewing ring. The apparatus is stitched to the sewing ring but can be disconnected by cutting a single suture. Preferably, the rotator and holder comprise a central rotator which is used first to protect and stabilize the leaflets of the heart valve during implantation and second to rotate the heart valve into a desired position after the sewing ring has been attached. A heart valve holder mounts on the rotator and is secured to the heart valve suture ring by a thread or suture. The holder may be integral with the rotator, but is preferably detachable. After the heart valve is stitched into the proper location in the heart, the attending physician cuts the suture at a single location and withdraws the heart valve holder, rotator and suture as a single component. If removable the heart valve holder, carrying both parts of the severed suture, is removed from the rotator. The rotator can then be returned to the heart valve to adjust the orientation of the annular valve body within the suture ring.

With the foregoing in mind, it is the object of my invention to provide a heart valve rotator and holder which can be secured to a mechanical heart valve having a rotatable suture ring by a single suture.

It is another object of my invention to provide such a combined structure which can be removed from the heart valve by severing the suture at a single point.

Another important object of my invention is to provide a heart valve holder and heart valve rotator and holder which retains the suture on the heart valve holder and rotator for complete withdrawal from the patient's body.

Another object of my invention is to provide a heart valve holder and rotator wherein the heart valve holder can be removed from the rotator and the rotator returned to the valve to adjust the orientation of the annular valve body within the sewing ring, thereby removing both the heart valve holder and suture from the field of operation.

These and further objects and advantages of my invention will be apparent from the following detailed description taken with reference to the accompanying drawings.

DETAILED DESCRIPTION OF MY PREFERRED EMBODIMENT

Figure 1:
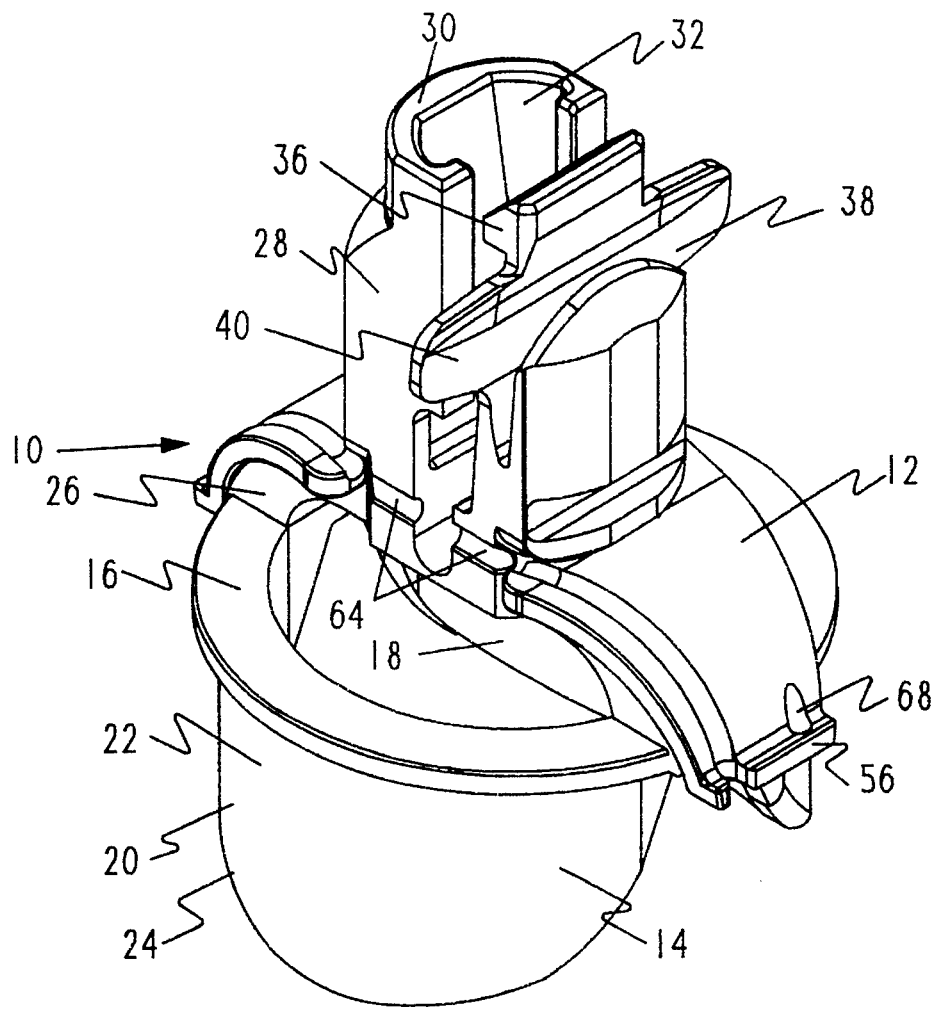
FIG. 1 is a perspective view of an heart valve holder and rotator combination in accordance with my invention.
Figure 2:
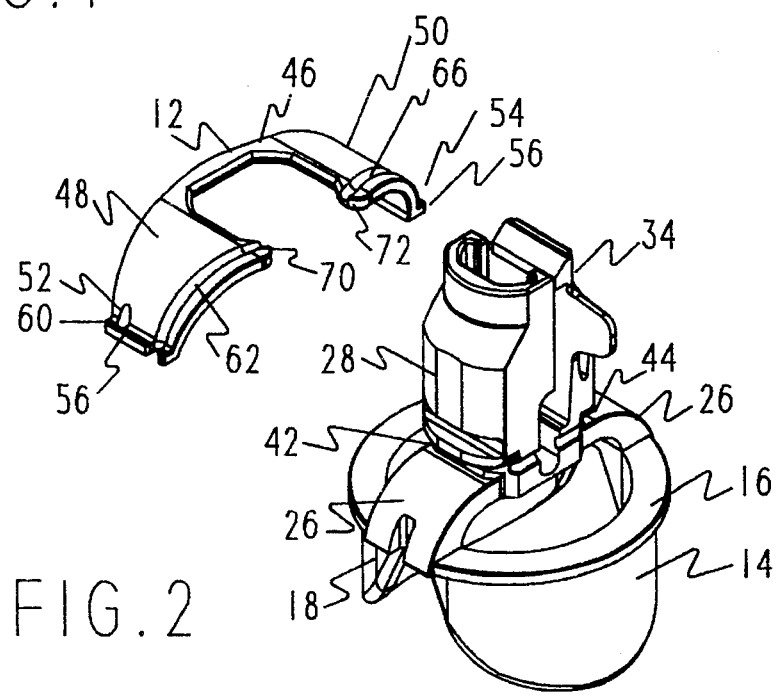
FIG. 2 is a perspective view of disassembled heart valve holder and rotator of FIG. 1.

I will now describe my preferred embodiment with reference to the accompanying drawings. FIG. 1 illustrates a combination 10 of a heart valve holder 12 and heart valve rotator 14. The heart valve rotator 14 comprises an annular rim 16 which supports right and left valve leaflet guards 18 and 20 respectively. One guard is provided for each leaflet of a heart valve. In the example shown here, a bileaflet heart valve is contemplated. However, valves with one, three or more leaflets are also known. It is within the scope of one skilled in the art to provide guards similar to the guards 18, 20 to conform with the selected geometry of the heart valve used with this apparatus. The guards, such as guards 20, comprise an arched surface 22 configured to extend along an inner wall of an annular valve body of a heart valve prosthesis. An arcuate lower edge 24 generally follows an outer edge of a leaflet of such a heart valve when the apparatus 10 is mounted thereon. The arcuate edge 24 of the rotator 14 extends, however, slightly beyond the heart valve leaflet, thus protecting the edge of the leaflet from damage.

A saddle 26 extends across the ring 16, connecting opposite sides of the ring. Centrally located along the saddle is a handle post 28, which extends away from the leaflet guards and thus would be away from the heart valve when the rotator is mounted on the valve. The handle post 28 comprises a rigid section 30 which has a central tapered cavity 32 configured to receive a handle (not shown). A movable portion 34 confronts the rigid portion 30. Proximally (that is, toward the user of the apparatus) the flexible portion 34 has a transverse tooth 36, configured to engage a slot (not shown) on the handle. Two wings 38, 40 are provided so that the flexible portion 34 can be pulled away from the handle, disengaging the tooth 36 from the slot and allowing the handle to be removed from the rotator. This configuration permits more efficient storage of the heart valve holder and rotator when mounted on a heart valve and sealed in sterile packaging. When the sterile packaging is removed in the operating theater, the handle can then be inserted into the rotator. The post 28 also comprises lips 42, 44 on the rigid post 30 and the flexible post 34 respectively. These lips are located distally on the post 28, adjacent the saddle 26. Preferably, the heart valve holder 12 slides onto the rotator 14 between the lips 42, 44 and the saddle 26, although it could also be permanently attached to the rotator.

The heart valve holder 12 comprises a curved body 46 configured to conform to the saddle 26. The curved body 46 has opposed arms 48, 50 which extend adjacent the ring 16 of the rotator. Ends 52, 54 of the arms 48, 50 respectively will lie adjacent the suture ring of a prosthetic heart valve when the combination is assembled. Each end 52, 54 has a flange 56, 58 respectively which extends radially outwardly. In each flange there is a through bore 50 through which a suture will be passed. The suture is tied to the heart valve holder 12 at the through bore 60 and then passed into the suture ring. The suture emerges from the suture ring into a groove 62 along the arm 48 and is passed across the post 28 of the rotator along a second groove 64. The suture then passes along a third groove 66 in the arm 50 and through the flange 56 into the suture ring. The suture emerges from the suture ring through a second bore 68 in the flange 56 and is there again secured to the heart valve holder.

In operation, the rotator protects the leaflets of the heart valve both by preventing motion of the leaflets and by extending beyond the edge of the leaflets preventing the impact of the leaflet edge during implantation. The heart valve holder 12, being secured to the sewing ring and to the rotator, prevents relative motion between the annular body of the heart valve and the sewing ring while implantation occurs. After the sewing ring has been stitched into the patient's heart, the physician can remove the heart valve holder and rotator by cutting the suture adjacent the post 28 and between the arms 48, 50. The integral heart valve holder and rotator 10 can then be removed from the heart valve with the two parts of the suture attached to the arms of the heart valve holder. When the holder and rotator have been removed from the valve and are withdrawn from the patient, the heart valve holder can be removed from the rotator by sliding it off the post 28. The holder is held onto the post by opposed tabs 70, 72 on the arms 48, 50 respectively. Elastic deformation of the holder allows the holder to be withdrawn from the post 28. Thus, the holder 12 retains the suture and can be safely removed from the operating area.

The rotator 14 can then be reinserted into the heart valve and the annular valve body can be rotated within the suture ring to the preferred orientation selected by the surgeon.

My invention may be embodied in other forms without departing from the spirit or teachings thereof and the foregoing description is intended in all respects to be illustrative. The scope of my invention is to be defined by the following claims.

I claim as my invention:

1. An apparatus for supporting a mechanical heart valve during implantation of the heart valve in a patient, the heart valve having an annular valve body, at least one leaflet within said annular valve body and adapted to pivot between open and closed positions, and a sewing ring circumferentially surrounding said annular valve body, the apparatus comprising
   a heart valve rotator having
      at least one leaflet guard adapted to extend within said annular valve body adjacent said leaflet, and
      a post connected to said guard and extending away from said valve body,
   a sewing ring holder connected to said heart valve rotator and extending adjacent said sewing ring at at least two distinct points on said ring, said holder having
      at least one arm extending between said sewing ring and said post, and
      means releasably connecting said holder to said post
   a single suture having
      a first end secured to said holder,
      a middle part releasably attached to said sewing ring at each of said distinct points, and
      a second end secured to said holder, said single suture holding said sewing ring holder and said heart valve rotator in contact with said heart valve and being reseasable from said heart valve by severing said suture at a single point into a first and second portion, said first portion including said first end and said second portion including said second end, whereby said first and second portions remain secured to said holder.

2. The apparatus according to claim 1 wherein said holder further comprises a first arm and a second arm, said first and second arms extending generally linearly along a diameter of said heart valve.

3. The apparatus according to claim 2 wherein said first end of said suture is secured to said first arm and said second end of said suture is secured to said second arm.

4. The apparatus according to claim 3 wherein said suture is stitched into said sewing ring adjacent said first arm, is passed along said first arm to said second arm, and is stitched into said sewing ring adjacent said second arm.

5. The apparatus according to claim 4 wherein said holder further comprises a groove extending along said first arm and along said second arm and wherein said suture passes along said groove from said suture ring adjacent said first arm to said suture ring adjacent said second arm.

6. An apparatus for supporting a mechanical heart valve during implantation of the heart valve in a patient, the heart valve having an annular valve body, at least one leaflet within said annular valve body and adapted to pivot between open and closed positions, and a sewing ring circumferentially surrounding said annular valve body, the apparatus comprising
   a heart valve rotator having
      at least one leaflet guard adapted to extend within said annular valve body adjacent said leaflet,
      a saddle connected to said leaflet guard adjacent said annular valve body at a first side thereof, extended diametrically across said valve body and connected to said leaflet guard adjacent said annular valve body at a second side thereof, and
      a post connected to said saddle and extending away from said valve body, said post being connected to said saddle between said first and second sides,
   a sewing ring holder connected to said rotator and extending adjacent said sewing ring and having at least a first arm and a second arm, said first and second arms extending generally linearly along a diameter of said heart valve between said sewing ring and said post and releasably connecting said holder to said post, said holder further having a groove extending along said first arm and along said second arm, and
   a suture having
      a first end secured to said first arm of said holder,
      a middle part releasably stitched into said sewing ring adjacent said first arm, passed along said groove from said first arm to said second arm, and stitched into said sewing ring adjacent said second arm, and
      a second end secured to said second arm of said holder.

7. The apparatus according to claim 6 wherein said first arm of said holder fits adjacent said saddle from said first side to said post and said second arm of said holder fits adjacent said saddle from said post to said second side.

8. The apparatus according to claim 7 wherein said suture passes adjacent said post to capture said post within said connector.

9. A method for securing a mechanical heart valve in an apparatus for manipulating said heart valve, the heart valve comprising a sewing ring, an annular valve body rotatably received within said sewing ring, and at least one leaflet pivotally received within said valve body, the method comprising the steps of inserting a rotator into said annular valve body, attaching a sewing ring holder to said rotator, said sewing ring holder having at least two ends adjacent distinct points on said sewing ring, tying a first end of a single suture to said sewing ring holder at a first end of said two ends thereof, releasably securing said suture to said sewing ring adjacent said first end of said two ends, passing said single suture along said sewing ring holder from said first end to a second end of said two ends of said sewing ring holder, releasably securing said suture to said sewing ring adjacent said second end and tying a second end of said suture to said sewing ring holder at said second end of said two ends thereof.

10. The method according to claim 9 wherein the step of securing the suture to the sewing ring comprises stitching said suture through said sewing ring.

11. The method according to claim 10 wherein the step of passing the suture along the sewing ring holder further comprises securing said rotator to said sewing ring holder.

* * * * *